(12) United States Patent
Mitchell et al.

(10) Patent No.: US 8,439,953 B2
(45) Date of Patent: May 14, 2013

(54) SPINAL STABILIZATION SYSTEM AND METHOD

(75) Inventors: Margaret E. Mitchell, Cedar Park, TX (US); Michael E. Landry, Austin, TX (US); Stephen H. Hochschuler, Dallas, TX (US); Richard D. Guyer, Plano, TX (US)

(73) Assignee: Zimmer Spine, Inc., Minneapolis, MN (US)

( * ) Notice: Subject to any disclaimer, the term of this patent is extended or adjusted under 35 U.S.C. 154(b) by 1170 days.

(21) Appl. No.: 11/779,762

(22) Filed: Jul. 18, 2007

(65) Prior Publication Data

US 2008/0140125 A1 Jun. 12, 2008

Related U.S. Application Data

(63) Continuation of application No. 10/200,024, filed on Jul. 19, 2002, now abandoned.

(60) Provisional application No. 60/306,765, filed on Jul. 20, 2001.

(51) Int. Cl.
*A61B 17/56* (2006.01)

(52) U.S. Cl.
USPC ........................................ 606/279; 606/246

(58) Field of Classification Search .......... 606/246–250, 606/253, 277, 279, 300, 76, 86 A, 86 B; 623/17.11, 623/17.16, 23.57, 23.6
See application file for complete search history.

(56) References Cited

U.S. PATENT DOCUMENTS

| | | | | |
|---|---|---|---|---|
| 4,554,914 A | * | 11/1985 | Kapp et al. | 606/86 A |
| 5,011,484 A | * | 4/1991 | Breard | 606/249 |
| 5,015,248 A | | 5/1991 | Burstein et al. | |

(Continued)

FOREIGN PATENT DOCUMENTS

| | | |
|---|---|---|
| FR | 2703239 | 10/1994 |
| GB | 780652 | 8/1957 |

(Continued)

OTHER PUBLICATIONS

International Search Report for PCT/US02/23143, May 12, 2002 (7 pages).

(Continued)

*Primary Examiner* — Eduardo C Robert
*Assistant Examiner* — David Comstock
(74) *Attorney, Agent, or Firm* — Seager, Tufte & Wickhem, LLC

(57) ABSTRACT

A spinal stabilization system may include a pair of structural members coupled to at least a portion of a human vertebra with connectors. Connectors may couple structural members to spinous processes. Some embodiments of a spinal stabilization system may include fasteners that couple structural members to vertebrae. In some embodiments, a spinal stabilization system provides three points of fixation for a single vertebral level. A fastener may fixate a facet joint between adjacent vertebrae and couple a stabilization structural member to a vertebra. Connectors may couple the structural members to the spinous processes of the vertebrae. Use of a spinal stabilization system may improve the stability of a weakened or damaged portion of a spine. When used in conjunction with an implant or other device, the spinal stabilization system may immobilize vertebrae and allow for fusion of the implant or other device with vertebrae.

17 Claims, 17 Drawing Sheets

U.S. PATENT DOCUMENTS

| | | | |
|---|---|---|---|
| 5,062,850 A | | 11/1991 | MacMillan et al. |
| 5,522,899 A | | 6/1996 | Michelson |
| 5,527,312 A | | 6/1996 | Ray |
| 5,578,034 A | | 11/1996 | Estes |
| 5,868,745 A | | 2/1999 | Alleyne |
| 5,876,457 A | * | 3/1999 | Picha et al. ............... 623/17.11 |
| 6,099,527 A | | 8/2000 | Hochschuler et al. |
| 6,132,464 A | | 10/2000 | Martin |

FOREIGN PATENT DOCUMENTS

| | | | |
|---|---|---|---|
| RU | 2117455 C1 | * | 8/1998 |
| SU | 988281 A | * | 1/1983 |
| WO | WO03/007829 A1 | | 1/2003 |

OTHER PUBLICATIONS

Lanz et al., "Managing Spinal Fractures and Luxations in Dogs," *Veterinary Medicine*, Nov. 2000, pp. 868-887.

Office Action issued in U.S. Appl. No. 10/200,024, mailed Apr. 7, 2006, 10 pages.

Office Action issued in U.S. Appl. No. 10/200,024, mailed Jun. 18, 2007, 13 pages.

International Preliminary Examination Report issued in International Patent Application No. PCT/US02/23143, mailed Mar. 22, 2004, 7 pages.

European Communication issued in European Patent Application No. 02756552.2-1526, Sep. 21, 2009, 5 pages.

* cited by examiner

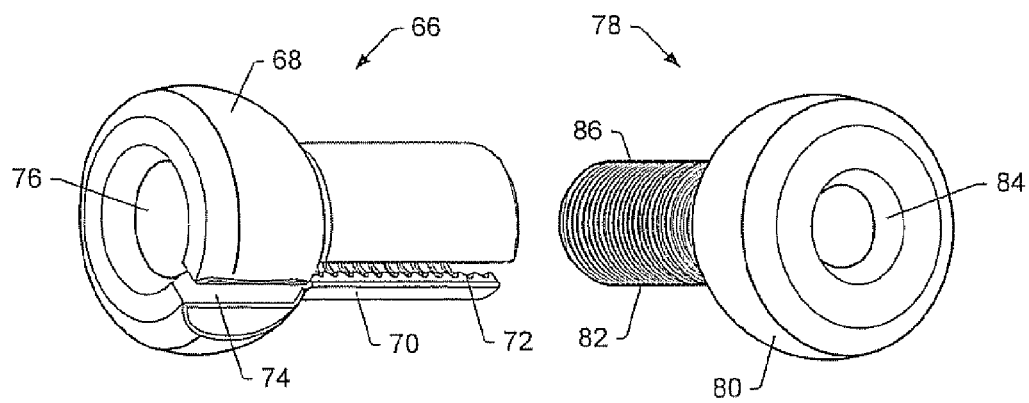
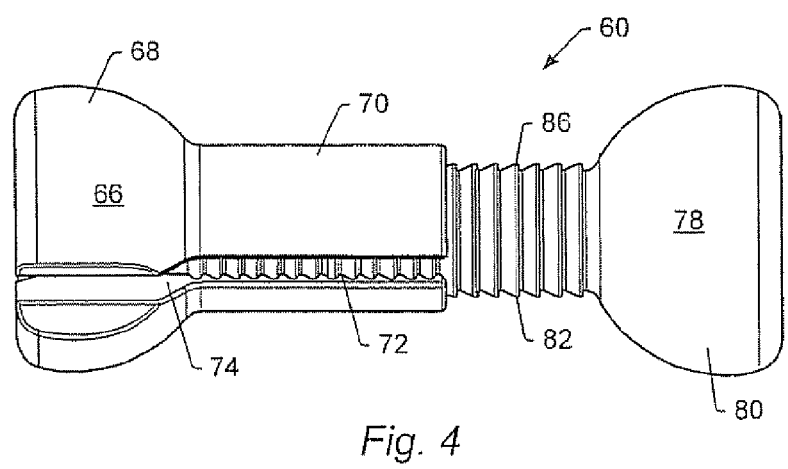

SPINAL STABILIZATION SYSTEM AND METHOD

PRIORITY CLAIM

This application is a continuation of U.S. patent application Ser. No. 10/200,024, filed Jul. 19, 2002 now abandoned, which claims priority to U.S. Provisional Application No. 60/306,765 entitled "Spinal Stabilization System and Method," filed Jul. 20, 2001; the above-referenced provisional application and non-provisional application are both incorporated by reference as if fully set forth herein.

BACKGROUND OF THE INVENTION

1. Field of the Invention

The present invention generally relates to the field of medical devices, and more particularly to a system for stabilizing a portion of a spinal column. In an embodiment, the system joins together adjacent spinous processes to stabilize a portion of a spine.

2. Description of Related Art

Spinal instability may result from many factors including trauma or degenerative disorders stemming from injuries and/or aging. In some instances, the effects of spinal instability may result in pain and/or partial or complete loss of mobility.

Several devices and techniques have been developed to restore stability to the spine. For example, interbody devices may be implanted within a prepared disc space to replace all or a portion of a damaged or compressed disc. To support the spine, vertebrae adjacent to a damaged or defective disc may be fused to each other with an interbody device or with interbody devices. In some instances, interbody devices alone may not be capable of supporting a portion of a spine sufficiently to promote vertebral fusion. A separate stabilization system may be required to improve stability of the spine or a portion of the spine.

One method of providing spinal stabilization utilizes a pedicle screw system. A pedicle screw system may stabilize one vertebra by connecting the vertebra to a second vertebra using anchoring pedicle screws and/or connecting rods or, plates. The connecting rods or plates may extend between the vertebrae. Pedicle screws are generally installed in pairs for each vertebral level that requires fixation. A pedicle screw is typically inserted into a pre-bored hole at the junction of a superior articular process and transverse process through the pedicle. A pedicle screw may be inserted in a craniolateral to caudomedial direction, depending on the particular region of the spine being stabilized.

Pedicle screw insertion is a technically demanding surgical procedure for spinal stabilization due to the close proximity of the spinal cord canal and/or major blood vessels. Complications may occur during the installation or use of pedicle screws for spinal stabilization or immobilization. Complications may include neural or dural damage as a result of pedicle screw penetration into the spinal canal or intervertebral foramen, pedicle screw bending and/or pedicle screw breakage. In addition, pedicle screw insertion may require highly invasive surgery. Such surgery may result in extended recovery times or even irreparable damage to adjacent tissues. Pedicle screws may be angulated in a craniolateral to caudomedial direction, depending on placement within the spine. Angulation of the pedicle screws may require a large exposure of the spine during insertion to accommodate desired trajectories of the pedicle screws.

Spinal stabilization may be established using braces attached to vertebrae. The braces may provide flexion/extension immobilization of the vertebrae. The braces may include plate systems positioned adjacent to the spine. Generally, plate systems are comprised of two opposing plates positioned on opposite sides of vertebral spinous processes. The plates may vary in size to accommodate variations in spinal anatomy.

To couple the plates to vertebrae, spinal plate systems may utilize nut and bolt assemblies positioned in pre-drilled holes in the plates. In some systems, the bolts are positioned in the space between the spinous processes of adjacent vertebrae. These systems may depend on a compressive force applied to the lateral sides of the spinous processes by the opposing plates to hold the system to the vertebrae.

U.S. Pat. No. 5,527,312 issued to Ray, which is incorporated by reference as if fully set forth herein, describes a system incorporating a facet screw anchor and fixation bar for immobilizing two vertebrae relative to each other. A portion of a fixation bar is wrapped around a portion of a superior vertebra pedicle. The fixation bar is secured to a facet screw anchor and the facet screw anchor is positioned through a facet joint of the superior vertebra and into the base of a transverse process of an inferior vertebra. The fixation bar and facet screw immobilize the superior vertebra and the inferior vertebra.

SUMMARY OF THE INVENTION

A spinal stabilization system may be used to increase stability of a portion of a spine. The spinal stabilization system may require a minimally intrusive surgical installation procedure. The spinal stabilization system may provide flexion/extension, torsion, and lateral bending stability to at least a portion of a spine. The system may be used as a stand-alone system or used in combination with other systems or devices.

A spinal stabilization system may include structural members positioned on opposite sides of a spinous process. A structural member may extend from a first vertebra to a second vertebra. The structural members may include openings on opposite sides of spinous processes of the vertebrae. The structural members may include texturing that allows a portion of the structural members to penetrate into spinous processes when the structural members are coupled to the spinous processes during an insertion procedure. In some embodiments, the texturing comprises spikes. Connectors may be positioned through openings in the structural members to couple the structural members to the spinous processes and to each other. The connectors provide a point of stabilization for the spinal stabilization system.

In some embodiments, structural members may include flanges having flange openings. Fasteners may be positioned through the flange openings. The fasteners may be positioned through facet joints of vertebrae being stabilized. A fastener on each side of a spinous process may provide two points of fixation for each vertebra. Structural members with flanges may be provided in mirror image pairs to fit on opposite sides of spinous processes.

Immobilizing a desired portion of a spine may require multiple structural members. A connector may couple a structural member to an adjacent structural member. In an embodiment, a connector may couple multiple structural members to a portion of a vertebra or vertebrae. A portion of a connector may pass through an opening in a structural member and through an opening in a spinous process of a vertebra. The connector may be positioned through a structural member and/or vertebral opening at an oblique angle relative to a centerline axis of the opening. A portion of a connector may abut an opening surface to inhibit continued axial movement of the connector through the opening during use. A punch tool and a connector tool may be used during an installation process. The punch tool may form an opening through a spinous process. A connector may be positioned through the opening to couple structural members positioned on opposite sides of spinous processes together. A connector tool may form a connector that joins the structural members together.

In a spinal stabilization system embodiment, the spinal stabilization system may include a pair of structural members positioned adjacent to opposing sides of a spinous process of a first vertebra. Openings may extend through the structural members to allow access to vertebral surfaces of the first vertebra from an outer surface of a structural member. Texture on a surface of a structural member may abut vertebral surfaces to provide a frictional and/or form coupling between the structural member and the vertebra. In some embodiments, portions of the texturing may penetrate into vertebral bone during installation.

Ends of a structural member may be placed adjacent to spinous processes of vertebrae to be stabilized. Openings in the structural member may abut openings through spinous processes. Connectors may be formed in openings to join together structural members positioned on opposite sides of the spinous processes.

A spinal stabilization system may be adapted to stabilize a portion of a spine where a spinous process is not present, has been damaged or removed, or is not capable of withstanding structural loads for spinal fixation. For example, a spinal stabilization system may provide or restore stability to the lumbosacral region of the spine. An artificial spinous process may be inserted to function as a spinous process for the stabilization system.

Spinal stabilization systems may stabilize more than one vertebral level. For example, a spinal stabilization system may couple a first vertebra to an adjacent second vertebra (one vertebral level). The second vertebra may be coupled to an adjacent third vertebra. The spatial and angular relationship between the first and second vertebrae and the second and third vertebrae may be different. A spinal stabilization system may maintain the natural spatial and angular relationship between the adjacent vertebral levels. In some embodiments, the spinal stabilization system may establish a desired spatial and angular relationship between adjacent vertebrae.

Fusion between vertebrae may be desirable for stabilization and permanent fixation of a portion of a spine. A spinal stabilization system may accommodate means for promoting bone growth between adjacent vertebrae. Bone graft may be placed adjacent to a structural member of a spinal stabilization system and the spinous processes of adjacent vertebrae coupled to the structural member to promote fusion between the vertebrae. Additionally, bone graft may be placed between an articular facet joint of adjacent vertebrae after removing the necessary soft tissue or exposing the inter-articular space. A fastener may be positioned through portions of the adjacent vertebrae and the facet joint to immobilize the joint and promote bone growth, A spinal fixation system may be used to substantially increase the stability of a portion of a spine containing an interbody fusion device and also relieve a significant amount of pressure on the interbody device.

BRIEF DESCRIPTION OF THE DRAWINGS

Advantages of the present invention will become apparent to those skilled in the art with the benefit of the following detailed description of embodiments and upon reference to the accompanying drawings in which:

FIG. 2 depicts an embodiment of a first member of a connector.

FIG. 3 depicts an embodiment of a second member of a connector.

FIG. 4 depicts an embodiment of an assembled connector.

Figure 1:
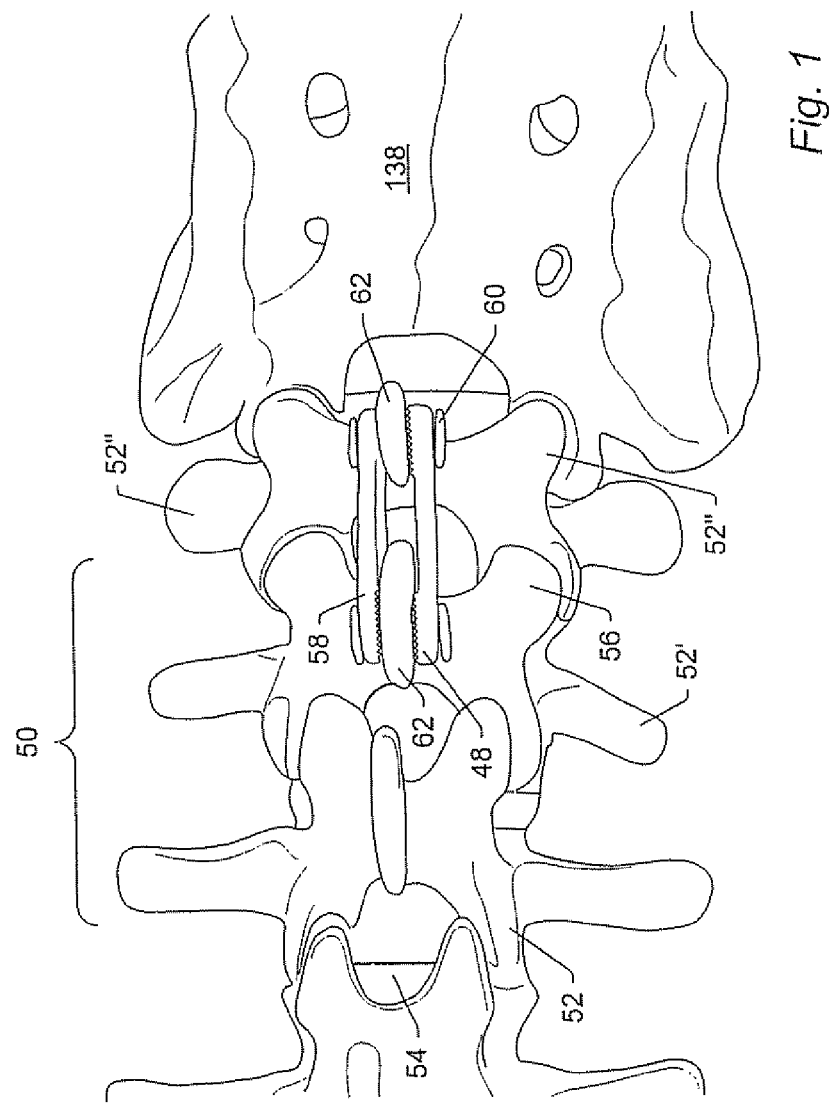
FIG. 1 depicts a posterior view of a portion of a spine with an embodiment of a spinal stabilization system for stabilizing a vertebral level.

While the invention is susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims.

DESCRIPTION OF PREFERRED EMBODIMENTS

A spinal stabilization system may provide stabilization for one or more vertebral levels of a spine. In some embodiments, a spinal stabilization system may be utilized as a stand-alone system. In some embodiments, a spinal stabilization system may be used in conjunction with other systems or devices to provide stability to the spine. For example, a spinal stabilization system may be used in conjunction with a spinal implant (e.g., an interbody fusion device, an artificial disc, and/or a vertebral construct). The spinal stabilization system may be easy to install with only minimal intrusion to adjacent tissue and muscle as compared to conventional stabilization systems. In addition, the spinal stabilization system may provide minimal risk of dural or neural damage during installation and use.

Appropriately sized spinal stabilization systems may be used to couple adjacent vertebrae of a spinal column. For example, an appropriately sized spinal stabilization system may be used to join an L2 vertebra to an L1 vertebra, or an L1 vertebra to a T12 vertebra.

FIG. 1 depicts an embodiment of spinal stabilization system 48. Spinal stabilization may be used to stabilize vertebral level 50. Vertebral level 50 may include two vertebrae 52, and intervertebral disc 54. Portions of vertebrae 52 may form bilateral facet joints 56.

In some embodiments, spinal stabilization system 48 may include structural members 58 and connectors 60. Structural members 58 may have a length that spans from spinous process 62 of a first vertebra to spinous process 62 of an adjacent vertebra that is to be fixed in position relative to the first vertebra. Structural members 58 may have a rod form or a bar form, or may have any other form able to withstand tensile, compressive, and/or torsion loads associated with the spine.

During uses structural members 58 may be coupled to each side of spinous processes 62. For example, spinal stabilization system 48 may be coupled to spinous processes 62 of the L4 vertebra 52' and the L5 vertebra 52". Connectors 60 may couple the structural members 58 to spinous processes 62. Connectors 60 may be any type of connector that couples structural members 58 together.

Structural members 58 may be formed in various sizes. The various sizes may accommodate different sizes of patients. Various sizes may also accommodate different sizes needed to stabilize different vertebrae. An instrument set supplied to a surgeon may include several different sizes of structural members. In some embodiments, structural members to be positioned on a left side of a spinous process may be substantially a mirror image of a structural member to be placed on a right side of a spinous process. An instrumentation set may include several different sizes of structural member pairs.

Structural members and connectors may be made of any biocompatible materials. Structural members and connectors may be formed of, but are not limited to being formed of, metals, ceramics, polymers, and/or composites. In some embodiments, structural members and connectors may be formed of titanium, titanium alloys, steel, and/or steel alloys. In some embodiments, structural members and/or connectors may be or may include bioabsorbable material.

In some embodiments, a shape of a structural member may be adjusted prior to insertion into a patient to conform to the patient's anatomy. The structural member may be capable of accommodating minor plastic deformation without altering the structural member's mechanical properties. Benders may be included in an instrumentation kit to allow structural members to be shaped.

In some embodiments, connectors 60 may be formed of a first member and a second member FIG. 2 depicts an embodiment of first member 66. First member 66 may include head 68, shark 70 having grooves 72 on an inner surface, slot 74, and tool opening 76. Head 68 may be larger than an opening in a structural member to inhibit passage of first member through the structural member.

In some embodiments, shank 70 of first member 66 includes a plurality of grooves 72 to engage a second member and form an interference fit that inhibits separation of the first and second members. In some embodiments, grooves 72 are female thread in the inner surface of shank 70. In some embodiments, shank 70 may include a single groove, a plurality of ridges, and/or a single ridge to couple the first member to a second member.

First member 66 may include slot 74 along a portion of a length of the first member. Slot 74 may allow first member 66 to radially expand during assembly of a connector.

Tool opening 76 may allow first member 66 to be coupled to a connector tool. First member 66 may be placed on a first arm of the connector tool. A second member may be placed on a second arm of the connector tool. The connector tool may be activated to bring the arms together and form a connector from first member 66 and the second member.

FIG. 3 depicts an embodiment of second member 78. Second member 78 may include head 80, shank 82, and tool opening 84. Head 80 may be larger than an opening in a structural member to inhibit passage of second member through the structural member. Tool opening 84 may allow second member 78 to be coupled to an arm of a connector tool.

In some embodiments, an outer surface of shank 82 may include a surface that engages and locks with a shank of a first member. In an embodiment, shank 82 includes a plurality of ridges 86 to engage grooves in a shank of the first member. In an embodiment, shank 82 includes male threading that is configured to engage female threading in inner surface of the shank of the first member. In other embodiments, shank 82 may include a single groove, a plurality of grooves, and/or a single ridge to couple the second member to a first member.

FIG. 4 depicts connector 60. Shank 82 of second member 78 may be pressed into shank 70 of first member 66 so that ridges 86 of the second member engage grooves 72 in the first member. The orientation of the ridges and grooves may inhibit separation of first member 66 from second member 78 when the first member and second member are coupled together. When first member 66 and second member 78 are coupled together, connector 60 is formed. Slot 74 may allow first member 66 to radially expand when ridged shank 82 is inserted into the first member. Ridges of second member 78 may engage grooves of first member 66 to inhibit separation of connector 601.

A structural member of a spinal stabilization system may include openings that accept a head of either first member 66 or second member 78. A punch tool may be used to form an opening through a spinous process. Structural members may be placed on each side of the spinous process so that the openings of the structural members align with the opening through the spinous process. First member 66 and second member 78 may be coupled to a connector tool. The connector tool may be used to couple first member 66 to second member 78 in openings through the structural members and the opening through the spinous process to form connector 60.

Figure 5:
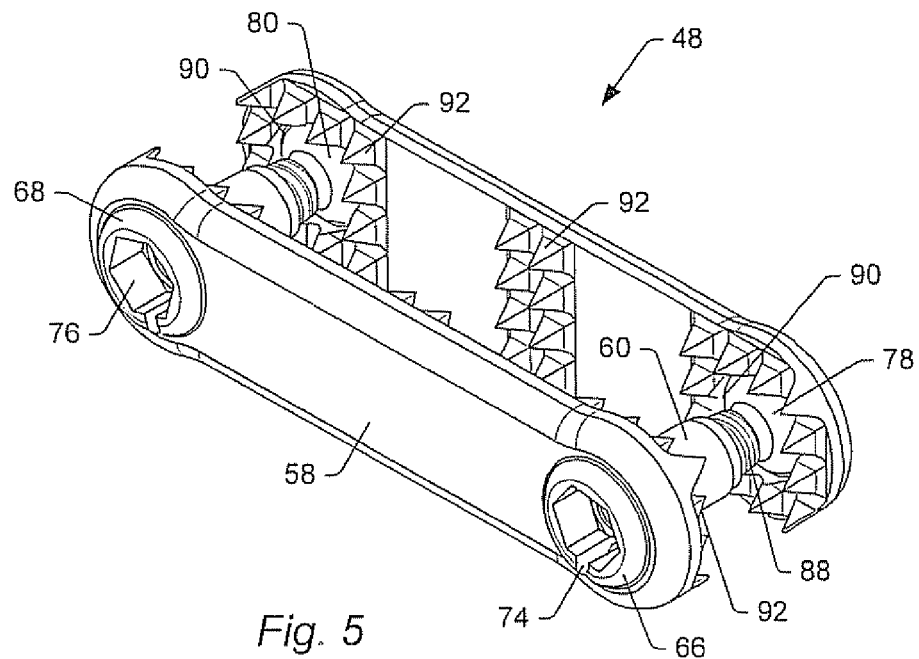
FIG. 5 depicts a perspective view of a spinal stabilization system.

FIG. 5 depicts a perspective view of spinal stabilization system 48. Connector 60 may include threading on an inside surface of first member 66 to engage threading 88 of second member 78. First member 66 may include slot 74 that allows the first member to expand when second member 78 is inserted into the first member to couple the first member to the second member. Second member 78 may be pressed into first member 66 using a connector tool. Threading of first member 66 and threading 88 of second member 78 may allow for removal of connector 60 from structural members 58. Tool openings may include slots, hexagonal openings, or other types of openings for engaging a drive tool (e.g., a ratchet drive) that allows for separation of the first member from the second member. Joining a connector together by pressing a second member into a first member may allow for simple and efficient formation of a spinal fixation system. The ability to separate the first member from the second member may allow for removal of a spinal fixation system or portions of the spinal fixation system should problems arise during an insertion procedure or at a later time.

In some embodiments, connectors 60 may be positioned within openings 90 in structural members 58. Connector 60 may be placed through structural member openings 90 in a direction that is substantially parallel to central axes of the openings. Openings 90 may allow a first portion of a connector to pass through the opening while inhibiting a head of the connector from passing through the opening. Heads 68, 80 of a first member and a second member may be too large to pass through structural member opening 90. Connectors may be used to join together two or more structural members to form spinal stabilization system 48.

Heads 68, 80 may have shapes that correspond to surfaces defining structural member openings 90. The shape of connector heads or fastener heads and the corresponding shapes of surfaces defined by openings in the structural members may allow connectors and/or fasteners to be positioned at desired angles relative to the structural members and vertebrae during an insertion procedure. The shape of openings 90 and the shape of heads 68, 80 may accommodate some misalignment between the openings of structural members 58.

Figure 6:
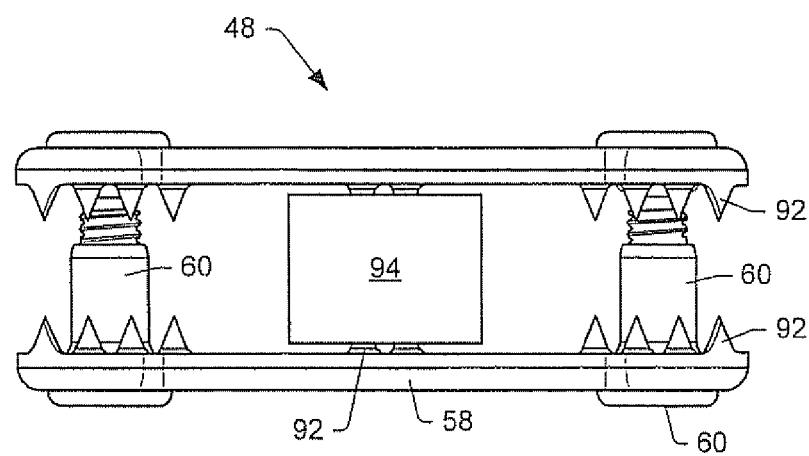
FIG. 6 depicts a top view of a spinal stabilization system.

As shown in FIG. 5 and FIG. 6, structural members 58 may include texturing 92. Texturing 92 may provide a secure connection between structural member 58 and a portion of a vertebra placed against the textured surface. The secure connection may inhibit movement of structural member 58 relative to the vertebra after the structural member and the vertebra are coupled together. Texturing 92 may include protrusions or roughening. For example, texturing 92 shown in FIG. 5 and FIG. 6 includes spikes. Texturing may include, but is not limited to, spikes, teeth, scoring, sharp particles implanted into surfaces of the structural members, ridges and grooves, and/or serrations. Surfaces of structural members that contact bone may include a coating of material to promote osseointegration of the structural member with bone. The coating may be, but is not limited to, a bone morphogenic protein, hydroxyapatite, and/or a titanium plasma spray.

When structural members 58 are coupled to vertebrae, texturing 92 may penetrate into spinous processes of the vertebrae. Some embodiments of structural member 58 may include texturing 92 at a position between ends of the structural member. Such texturing may be used to secure an implant between structural members. FIG. 6 depicts implant 94 positioned between structural members 58. Implant 94 may be a portion of bone or other graft material for promoting fusion of the spinous processes that the structural members are coupled to.

Some embodiments of spinal stabilization systems may use fasteners to couple vertebrae together. In some embodiments, an end of a spinal stabilization system may be coupled to vertebrae using fasteners, and a second end of the spinal stabilization system may be coupled to a spinous process of a vertebra using a connector. In some embodiments, each end of a spinal stabilization system may be coupled to a spinous process using a connector, and fasteners may be positioned through facet joints of the vertebrae.

Fasteners may include, but are not limited to, screws, nails, rivets, trocars, pins, and barbs. In an embodiment, the fasteners are bone screws. A length of a fastener may allow the fastener to engage multiple vertebrae. In an embodiment, a fastener may include a head and a shaft extending from the head. A portion of a tool may be inserted into an indention in the fastener head to position and insert the fastener. The size of the fastener head may inhibit the fastener head from passing through a structural member opening. A portion of a fastener head may substantially mate with a portion of an opening wall in a structural members. The mating surfaces may be textured to help keep the fastener angle fixed relative to the structural member. The shape of the fastener head may allow the fastener to be inserted through the opening at an oblique angle and support loads to secure the fastener within the opening. A length of a fastener shaft may allow the fastener to be positioned through a portion of a vertebra and into an adjacent vertebra. A fastener shaft may have threading or a series of ridges and grooves to secure the fastener to a vertebra or vertebrae. Alternatively, surface roughness may be provided on a fastener shaft to secure the fastener to adjacent surfaces.

Figure 7:
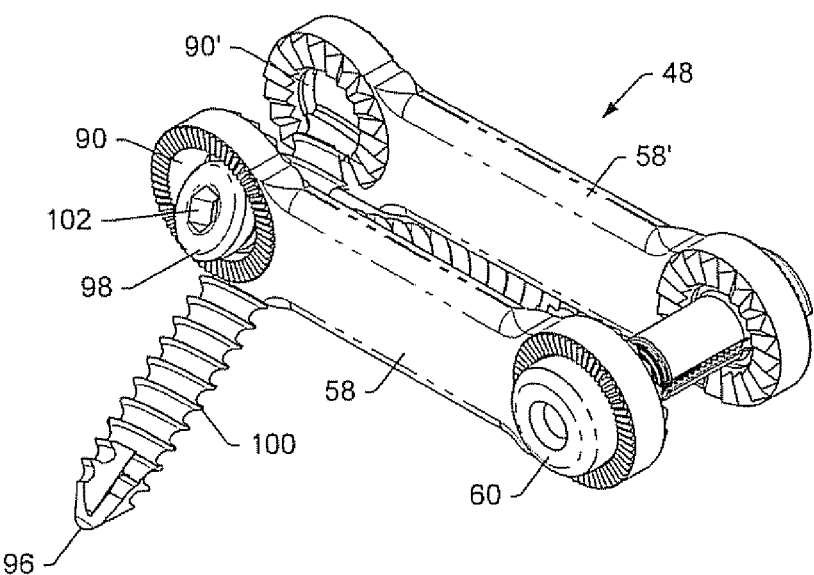
FIG. 7 depicts a perspective view of a spinal stabilization system.
Figure 8:
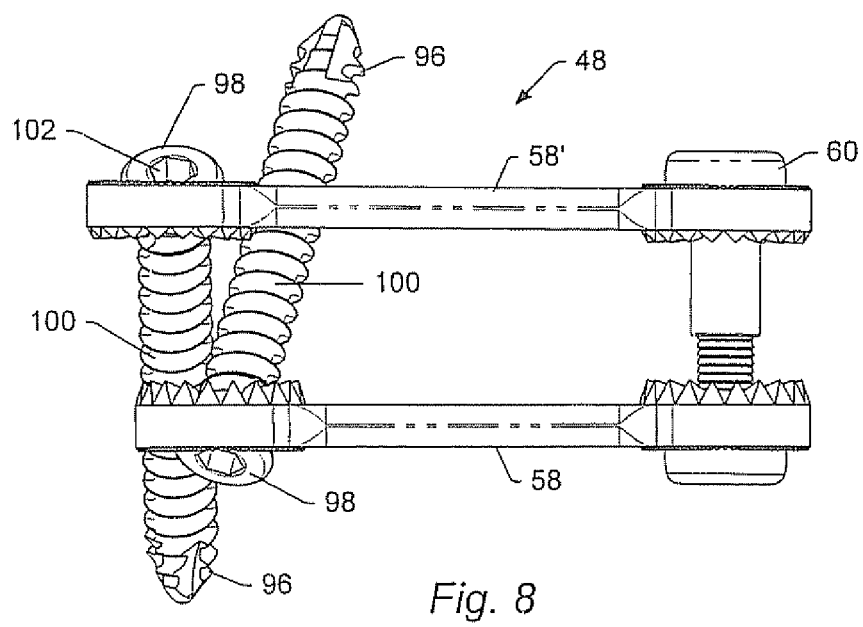
FIG. 8 depicts a top view of a spinal stabilization system.

Embodiments of spinal stabilization systems that use fasteners are depicted in FIG. 7 and FIG. 8. Spinal stabilization system 48 may include a fastener for coupling a portion of a first vertebra to a portion of a second vertebra and/or a portion of a vertebra to a structural member. Fasteners 96, such as the fasteners shown in FIG. 7 and FIG. 8, may include heads 98 and shanks 100. An outer dimension of fastener head 98 may be greater than an outer dimension of shanks 100. Shanks 100 may be sized to pass through openings in structural members. Heads 98 may be larger than openings to inhibit complete passage of a fastener through an opening in a structural member. Fastener head 98 may include indention 102 for the insertion of a portion of a tool used to drive fastener 96.

Spinal stabilization system 48 may include structural members 58 and 58', connector 60, and fasteners 96. Structural members 58 and 58' may include openings for fasteners and/or connectors to engage vertebrae or other structural members. Fasteners 96 and/or connectors 60 may be positioned through openings at angles oblique to a centerline axis of the openings. Structural members 58 and 58' may include texturing or protrusions on surfaces adjacent to vertebrae and/or adjacent to other structural members to provide form and/or friction coupling to the adjacent surfaces.

During use, a portion of structural member 58 may be positioned adjacent the spinous process of a first vertebra and a second portion of structural member 58 may be positioned adjacent a spinous process of a second vertebra. Opposing structural member 58' may be positioned along the opposite side of the spinous processes of the first and second vertebrae. Fasteners 96 may be positioned through an opening of structural member 58, through a lamina of the first vertebra, and through an articular facet joint of the first and second vertebrae to couple structural member 58 to the vertebrae and fixate the articular facet joint between the first and second vertebrae. Fasteners 96 may be positioned through an opening, through the opposite lamina of the first vertebra, and through a second articular facet joint of the first and second vertebrae. Connector 60 may couple structural members 58 and 58' to the spinous process of the second vertebra. In some embodiments, structural members 58 and 58' may have differing lengths to allow fasteners 96 to engage the vertebrae.

Figure 9:
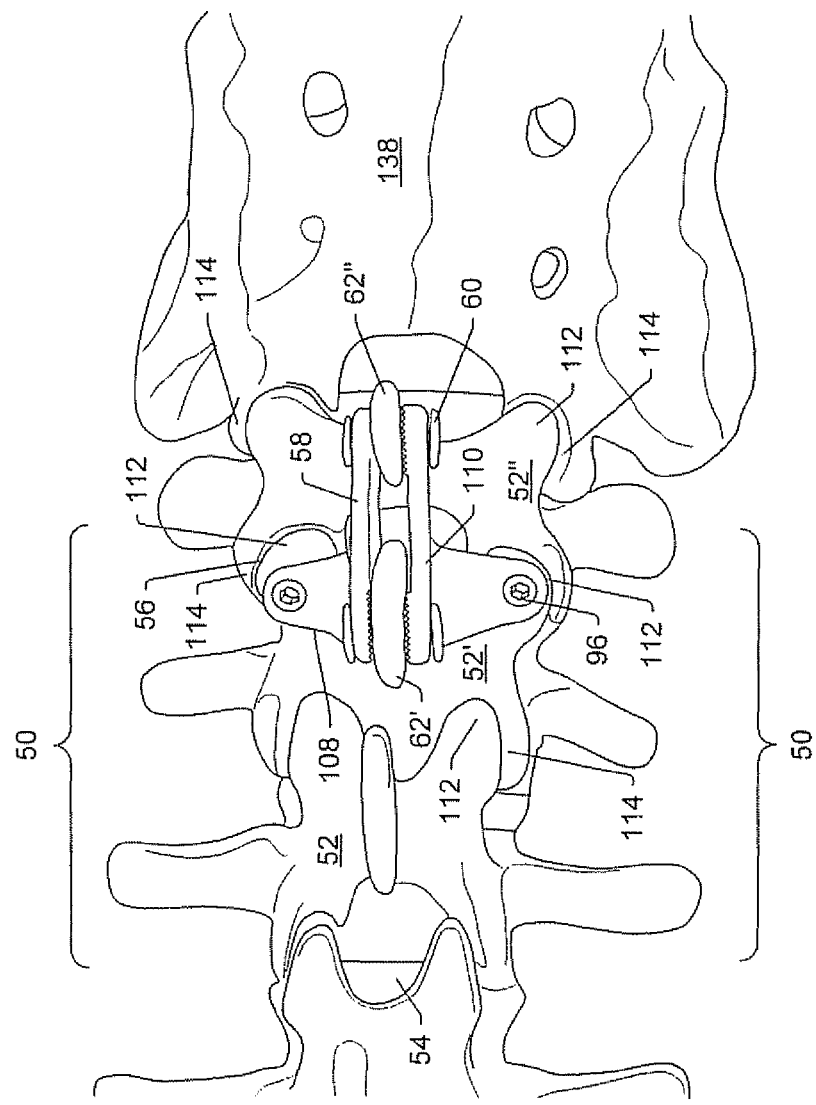
FIG. 9 depicts a posterior view of a portion of a spine with an embodiment of a spinal stabilization system for stabilizing a vertebral level.

FIG. 9 depicts an embodiment of a spinal stabilization system. Structural members 58 may include flange 108, elongated portion 110, and openings for connectors 60. A portion of flange 108 may be positioned adjacent to an articular process and facet of a first vertebra during use. In some embodiments, a portion of a bottom surface of a flange may include texturing that couples the flange to a vertebral body. The texturing may include, but is not limited to, scoring, protrusions, spikes, serrations, and/or particles embedded in the surface. Elongated portion 110 may have a length that spans from a spinous process of the first vertebra to a spinous process of an adjacent vertebra to be fixed in position relative to the first vertebra.

Connectors 60 and fasteners 96 may affix the structural members 58 to vertebrae. For L4 vertebra 52', structural members 58 attach to spinous process 62', and to each inferior articular process 112. For L5 vertebra 52", spinal stabilization system 48 attaches to spinous process 62", and to each superior articular process 114.

Figure 10:
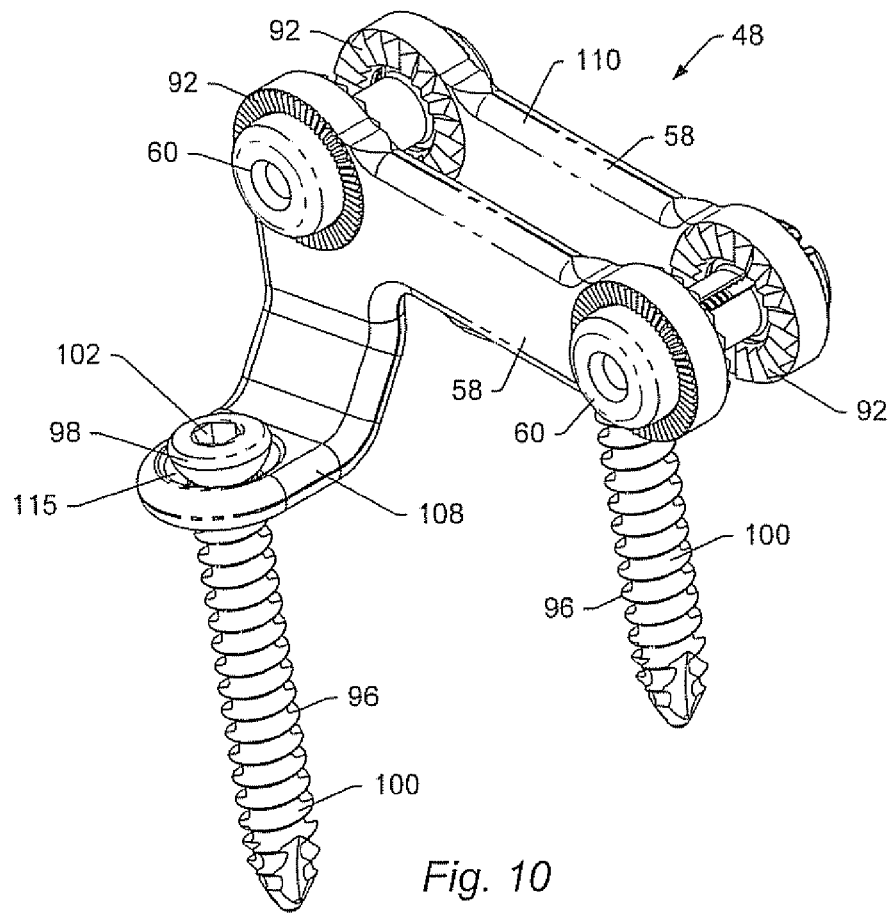
FIG. 10 depicts a perspective view of an embodiment of a spinal stabilization system.
Figure 11:
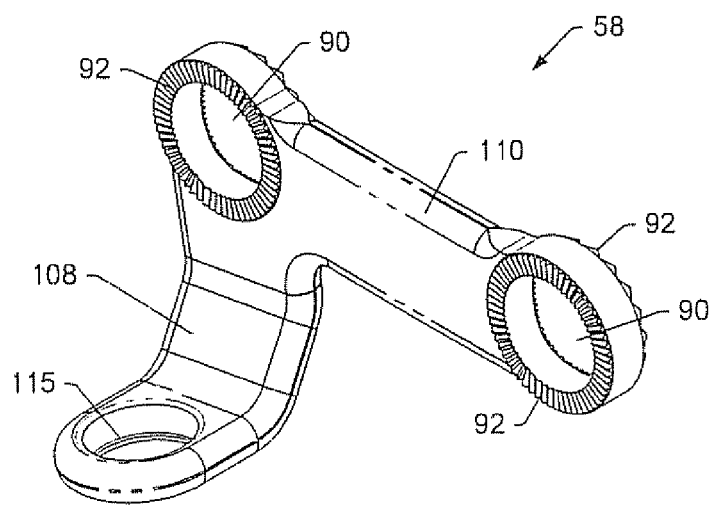
FIG. 11 depicts an embodiment of a structural member.
Figure 14:
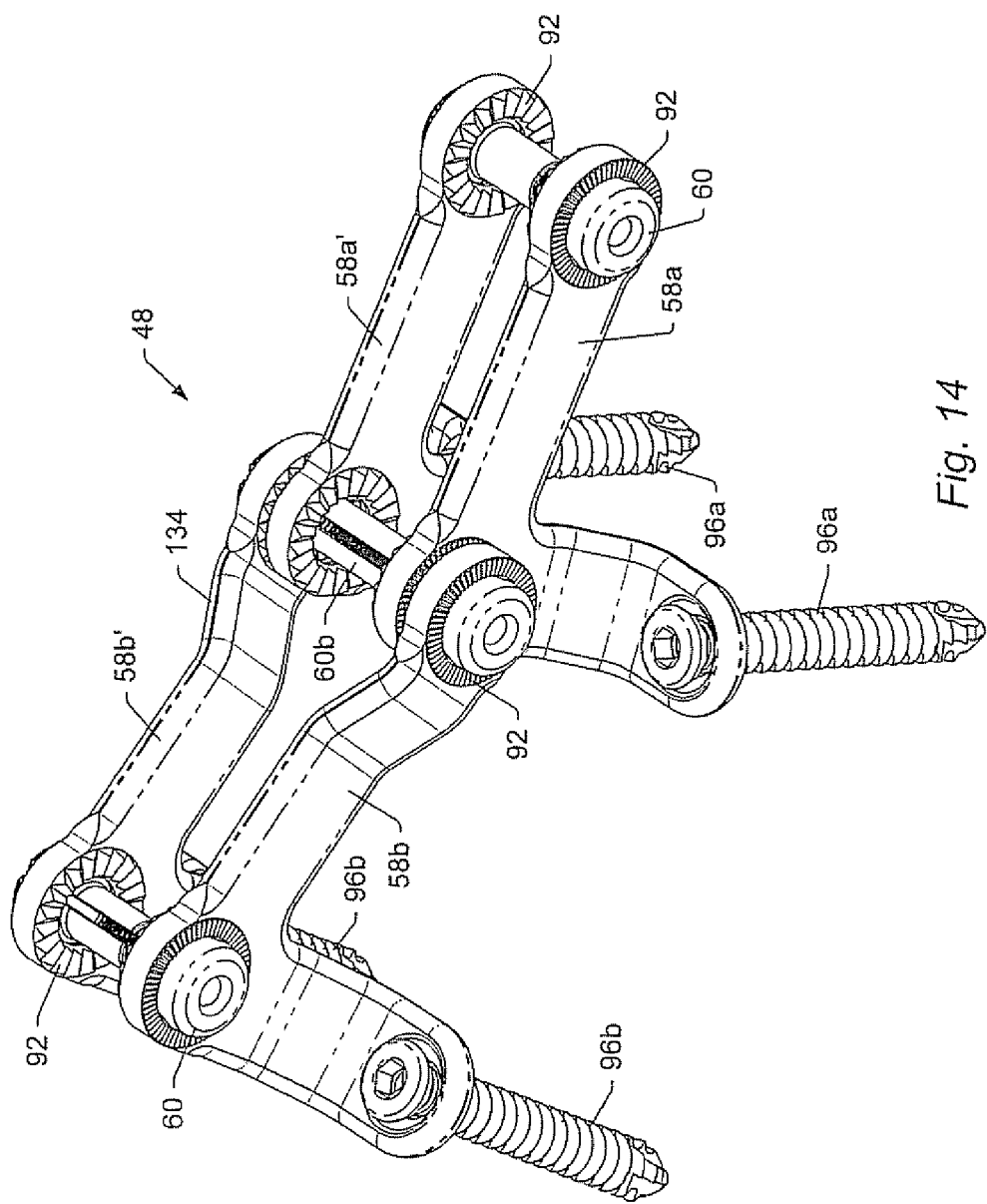
FIG. 14 depicts a perspective view of an embodiment of a multi-level spinal stabilization system.

FIG. 10 depicts a perspective view of an embodiment of spinal stabilization system 48. FIG. 11 depicts an embodiment of a structural member used to form spinal stabilization system 48. Structural member 58 may include texturing 92 adjacent to openings 90. Texturing on a side of structural member 58 away from flange 108 may enter vertebral bone during installation to help secure the structural member to the vertebrae. Texturing 92 on a side of structural member towards flange 108 may allow a frictional or, interference fit to be formed between a first structural member and a second structural member that abuts the first structural member to form a multi-level construct (e.g., as shown in FIG. 14). Texturing may promote fixation of a desired angle between portions of a multilevel construct that stabilize different vertebral levels.

In some embodiments, a structural member of a multi-level construct may span over vertebral level. A structural member may be coupled to 3 or more spinous processes to stabilize a portion of the spine. For example, a structural member for stabilizing two vertebral levels may include two openings proximate ends of the structural member, as well as an opening proximate a midpoint of the structural member. The openings may be positioned such that connectors and/or fasteners can be used to couple the structural member to the adjacent spinous processes. In some embodiments, the structural member may include texturing. Texturing may be used to engage a portion of a vertebra, an additional structural member, and/or an implant (e.g., bone graft). For example, a structural member may include spikes to engage a spinous process.

Figure 12:
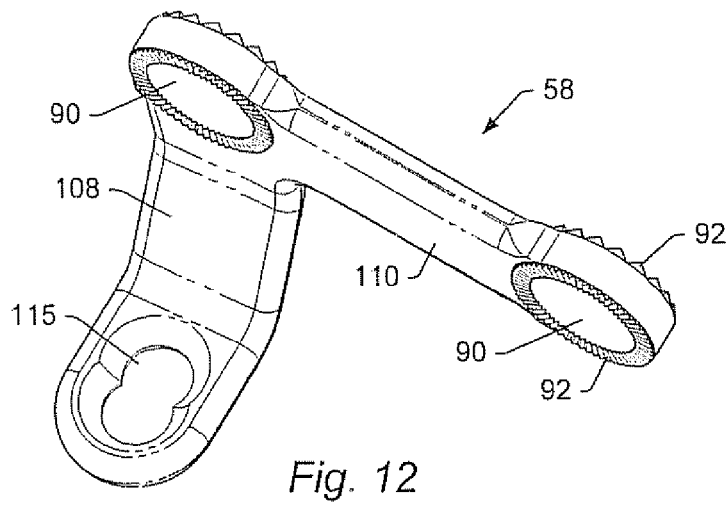
FIG. 12 depicts a perspective view of an embodiment of a structural member having an elongated opening.

As illustrated in FIG. 12, a first portion of flange opening 115 may overlap a second portion of the opening. The overlapping opening portions may provide options for placement of a fastener during an insertion procedure. In some embodiments, flange opening 115 may include only a single portion, two overlapping portions, or more than two overlapping portions. In some embodiments, a flange opening may include an elongated slot instead of overlapping portions. Openings 90 in structural member 58 for connectors in elongated portion may include overlapping portions or elongated slots that provide options for positional placement of the connectors.

Figure 13:
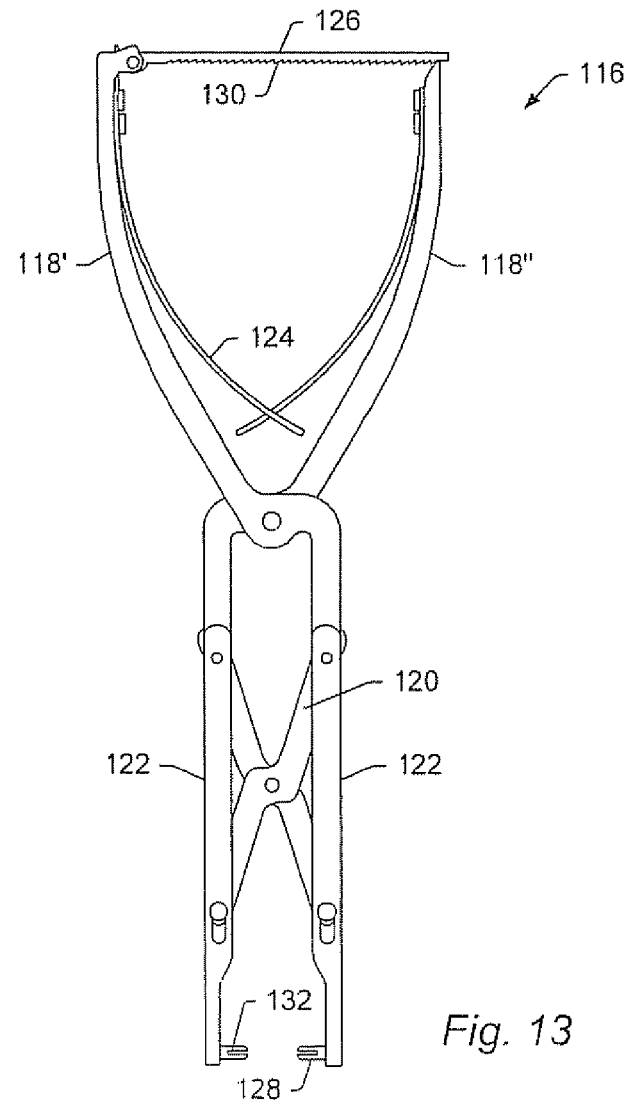
FIG. 13 depicts a front view of an embodiment of a connector tool

FIG. 13 shows a front view of an embodiment of connector tool 116 for inserting a connector. Insertion instrument 116 may include handles 118', 118", linking mechanism 120, arms 122, spring 124, ratchet arm 126, and holders 128. Linking mechanism 120 may allow holders 128 that are attached to arms 122 to approach each other from an open position with a small, or ino, rotational component of motion when handles 118 are squeezed towards each other. A first member and a second member of a connector may be placed on holders 128. A shank of the second member may be placed in a shank of the first member when handles 118 are squeezed together. Ratchet arm 126 may be rotatively attached to first handle 118'. Teeth 130 of ratchet arm 126 may engage an end of second handle 118". Teeth 130 may be oriented to allow handles 118 to approach each other when the handles are squeezed, but the teeth may inhibit the handles from returning to the open position. Spring 124 may apply force to handles 118 that forces the handles to the open position. When connector members are coupled together, ratchet arm 126 may be rotated away from the end of second handle 118" to allow spring 124, and/or a controlled release of pressure applied to handles 118, to return the insertion instrument to the open position.

Tool openings 76 and 84 of connector members 66, 78 (shown in FIG. 2 and FIG. 3) may be attached to holders 128 of insertion instrument 116. Holders 128 may include slots 132, O-rings, or another type of mechanism that allows the connector members to be securely attached to the holders. Slots 132 of holders 128 may be compressed when connector members are attached to the holders. Force applied by expansion of holders 128 against connector members 66, 78 may hold the connector members on the holders with enough force to inhibit unintentional removal of the connector members from the holders. After connector members 66, 78 are joined together by squeezing handles 118 of insertion instrument 116, holders 128 may be removed from tool openings 76, 84. The force applied by expansion of holders 128 against connector members 66, 78 may be significantly less than a force that resists separation of joined connector members so that the holders may be easily removed from tool openings 76 and 84 of formed connector 60.

In some embodiments of spinal stabilization systems, connectors may not be used to join structural members together. For example, in an embodiment, an adhesive may be used to bind structural members to a spinous process or to spinous processes. Using an adhesive may avoid the need to form an opening through a spinous process or spinous processes.

Structural member 58 may include a flange and an elongated portion. In some embodiments, the structural member is made of a single piece of material. In some embodiments, structural member 58 is made of a number of separate pieces that are joined together. The flange may be joined to the elongated portion by any method that provides a connection between the flange and the elongated portion that is able to withstand tensile, compressive, and/or torsion loads associated with the spine (e.g., by adhesion or by welding). In some embodiments, the elongated portions may be formed from plate stock, bar stock, or rod stock. Flanges may be formed from plate stock. In some embodiments, structural members 58 may be cast, molded, or otherwise formed as a single piece.

In some fastener embodiments, a fastener may include a break-off extension. The break-off extension may couple to a tool. The break-off extension may separate from a remaining portion of the fastener when enough force has been applied to the fastener to insert the fastener in bone. Use of a break-off extension may inhibit over-tightening of fasteners that results in the stripping of threading in the bone.

In some fastener embodiments, an expandable ring may be inserted in a structural member. Rings may be compressed and inserted into openings in structural members. After insertion, the rings may expand. Expansion of the rings may allow the rings to be coupled to the structural members to inhibit removal of the rings from the openings without the rings becoming secured to the structural members. A shank of a fastener may be inserted through a ring and into bone. A portion or portions of the ring may expand as a head of the fastener is inserted into the bone. After passage of a portion of the fastener into bone, a wide section of the head may pass beyond the portion or portions of the ring. Passage of the wide section of the head beyond the portion or portions may allow the portions or portions to contract. The portions may inhibit removal of the fastener from the structural member without fixedly binding the ring to the structural member and without fixedly binding the ring to the fastener.

In some fastener embodiments, shank 100 of fastener 96 may be threaded for securing the fastener to a portion of a vertebra or vertebrae. In alternative embodiments, a fastener may include texturing, or ridges and grooves, to provide friction and/or form coupling to secure a fastener to a portion of a vertebra. Threading of fastener 96 may be self-tapping to avoid the need for pre-boring and tapping of an opening in the vertebra. In some embodiments, holes may be bored and/or tapped in the vertebra to accommodate threading of fastener 96.

Shank 100 of fastener 96 may be positioned through a structural member opening at an oblique angle relative to a centerline axis of the opening in the structural member. A portion of fastener head 98 may be shaped to complement a portion of a flange opening. FIG. 10 depicts shanks of fasteners inserted through flange openings in structural member 58. A fastener may pass through a facet joint formed by an inferior articular process of a first vertebra and an adjacent superior articular process of a second vertebra to provide a point of fixation between structural member 58 and the first and second vertebrae.

FIG. 14 depicts an embodiment of spinal stabilization system 48 for stabilizing more than one vertebral level. A multi-level stabilization system may include multiple structural members that join vertebral levels. Using a multi-level spinal stabilization system that includes multiple structural members may allow for preservation of the natural curvature of the spine. The structural members may be coupled to each vertebral level using fasteners and/or connectors. In addition, a structural member may be coupled to another structural member using fasteners and/or connectors.

Spinal stabilization system 48 for stabilizing multiple vertebral levels may include structural members 58, connectors 60, and fasteners 96. Structural members 58a and 58a' may be positioned on opposing sides of the spinous processes of a first vertebra and a second vertebra. Structural members 58a and 58a' may be coupled to the first and second vertebrae using fasteners and connectors. Structural members 58b and 58b' may be positioned on opposing sides of spinous processes of the second vertebra and a third vertebra. Structural members 58b and 58b' may be coupled to the second and third vertebrae using fasteners and connectors. Connector 60b may couple structural members 58a, 58b, 58a', and 58b' to the spinous process of the second vertebra. Structural members 58, fasteners 96, and connectors 60 provide up to three points of fixations for each vertebral level. Additional structural members may be included in a spinal stabilization system for fixating additional vertebral levels.

A portion of structural member 58a may abut a portion of structural member 58b, and a portion of structural member 58a' may abut a portion of structural member 58b'. Openings in structural members 58a, 58b and openings in structural members 58a', 58b' may substantially align to allow connector 60b to be positioned through the openings to connect the structural members to the spinous process of the second vertebra. Structural member 58b and 58b' may include bends 134. Bends 134 may allow portions of structural members 58b and 58b' with openings to be positioned substantially parallel to structure members 58a and 58a' to maintain proper lateral alignment of the adjacent vertebrae.

Structural members 58a, 58b, 58a', and 58b' may include texturing 92 on selected surfaces. Texturing 92 may secure structural members 58a and 58b together by forming a friction or form lock between the structural members. Texturing 92 may inhibit rotation of a structural member about the contact point between the structural members. In a structural member embodiment, texturing 92 is radial serrations around an opening. Serrations on structural member 58a may engage serrations on structural member 58b to inhibit rotation of structural member 58a relative to structural member 58b.

Figure 15:
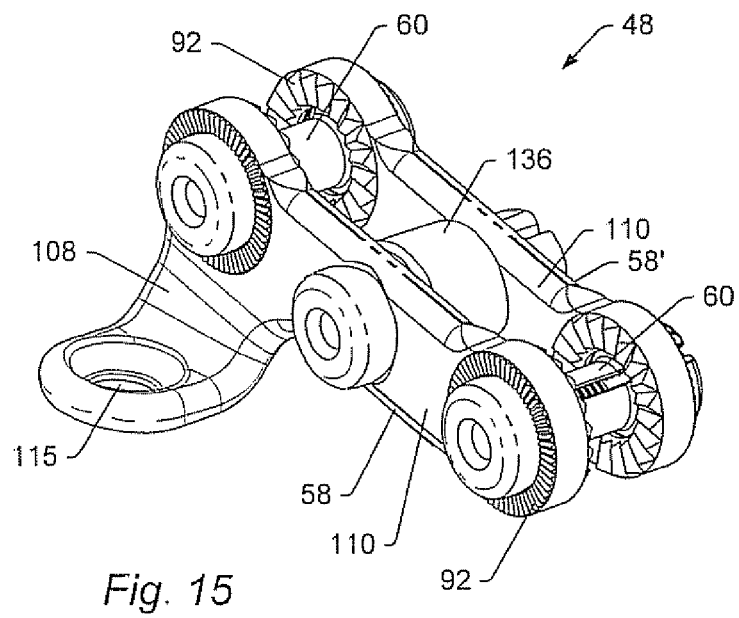
FIG. 15 depicts a perspective view of an embodiment of a spinal stabilization system having an interconnecting spacer.

A spinal stabilization system may include an intermediate spacer and/or connector to provide additional structural support for fixating adjacent vertebral levels. An embodiment of spinal stabilization system 48 using an intermediate spacer and connector is depicted in FIG. 15. Spacer 136 may provide additional structural support for elongated portions 110 of structural members 58 and 58'. Spacer 136 may be coupled to structural members 58 and 58' using a connector. Openings in structural members 58 and 58' may be aligned to allow spacer 136 to be positioned in a space between structural members 58 and 58'.

In some spinal stabilization system embodiments, a spacer and connector may be used instead of connectors positioned through a spinous process. Portions of structural members positioned adjacent to spinous processes may include texturing. In an embodiment, the texturing is a protrusion or protrusions that will extend into the spinous processes when a connector joins structural members positioned on opposite sides of the spinous processes. A first structural member may be positioned on a first side of spinous processes of adjacent vertebrae. A first fastener may be positioned through an opening in the first structural member and through a first facet joint of the vertebrae to join the vertebrae together. A second structural member may be placed on a second spinous process. A spacer may be positioned between the structural members. A connector may be formed through the structural members and the spacer to join the structural members together. Joining the structural members together may extend protrusions adjacent to the spinous processes into the spinous processes. A second fastener may be positioned through an opening in the second structural member and through a second facet joint of the vertebrae to join the vertebrae together.

Figure 16:
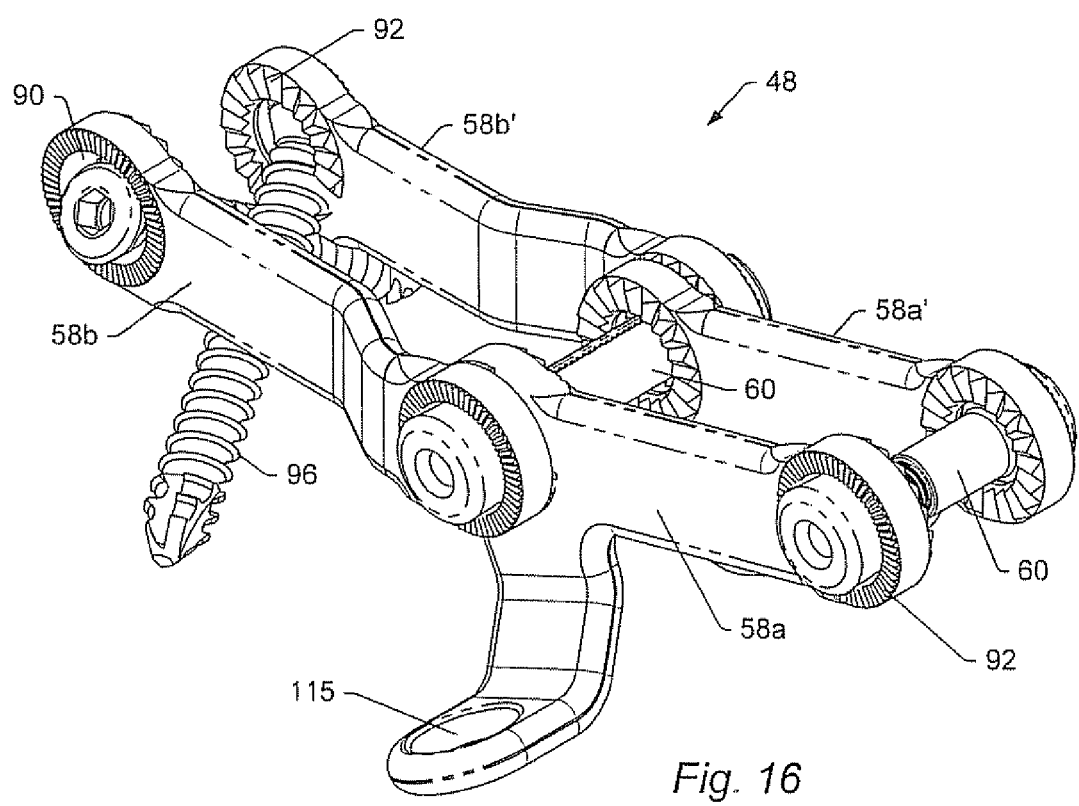
FIG. 16 depicts a spinal stabilization system for use in stabilizing more than one vertebral level.

FIG. 16 depicts spinal stabilization system 48 for use in stabilizing more than one vertebral level of a spine wherein the contours of a vertebral level do not allow for a proper angle of approach for fixating a facet joint between adjacent vertebrae. Openings 90 in structural members 58 may be adapted to receive fastener 96 for fixating a first vertebral level with a second vertebral level. Fastener 96 may be positioned through opening 90 to engage the spinous process of a first vertebral level. A length of fastener 96 may allow the fastener to pass through the spinous process, lamina and articular process, and facet of a first vertebral level to engage a portion of a second vertebra. Fastener 96 may be positioned through the lamina of the first vertebra and the lamina of the second vertebra to substantially provide a translaminar-facet coupling in addition to the spinous process coupling to the structural member. Fastener 96 may immobilize the facet joint between the vertebrae and provide an additional point of fixation for each vertebra. Serrations on a surface of structural member 58a may engage mating serrations on structural member 58b to couple the structural members to each other. Connectors 60 may be positioned through openings in structural members 58a, 58a', 58b, 58b' to engage the spinous process of the second vertebral level. Additional fasteners and/or connectors may fixate the structural members to other portions of the second or third vertebral level.

A spinal stabilization system may be adapted to portions of a spine wherein coupling to a spinous process of a vertebral level may not be desirable or achievable. Such situations occur when a spinous process for a vertebral level does not exist, is damaged, has been removed, or is determined to be incapable of supporting the loads associated with spinal fixation. For example, a spinal stabilization system may be adapted to stabilize a lumbosacral portion of the spine where the vertebra anatomically lacks a spinous process (e.g., the sacrum). FIG. 17 through FIG. 25 depict embodiments of spinal stabilization systems used to stabilize a portion of the spine that does not include a spinous process. If the existing spinous process is weak or damaged, the spinous process may be removed to allow for insertion of the spinal stabilization system.

Figure 17:
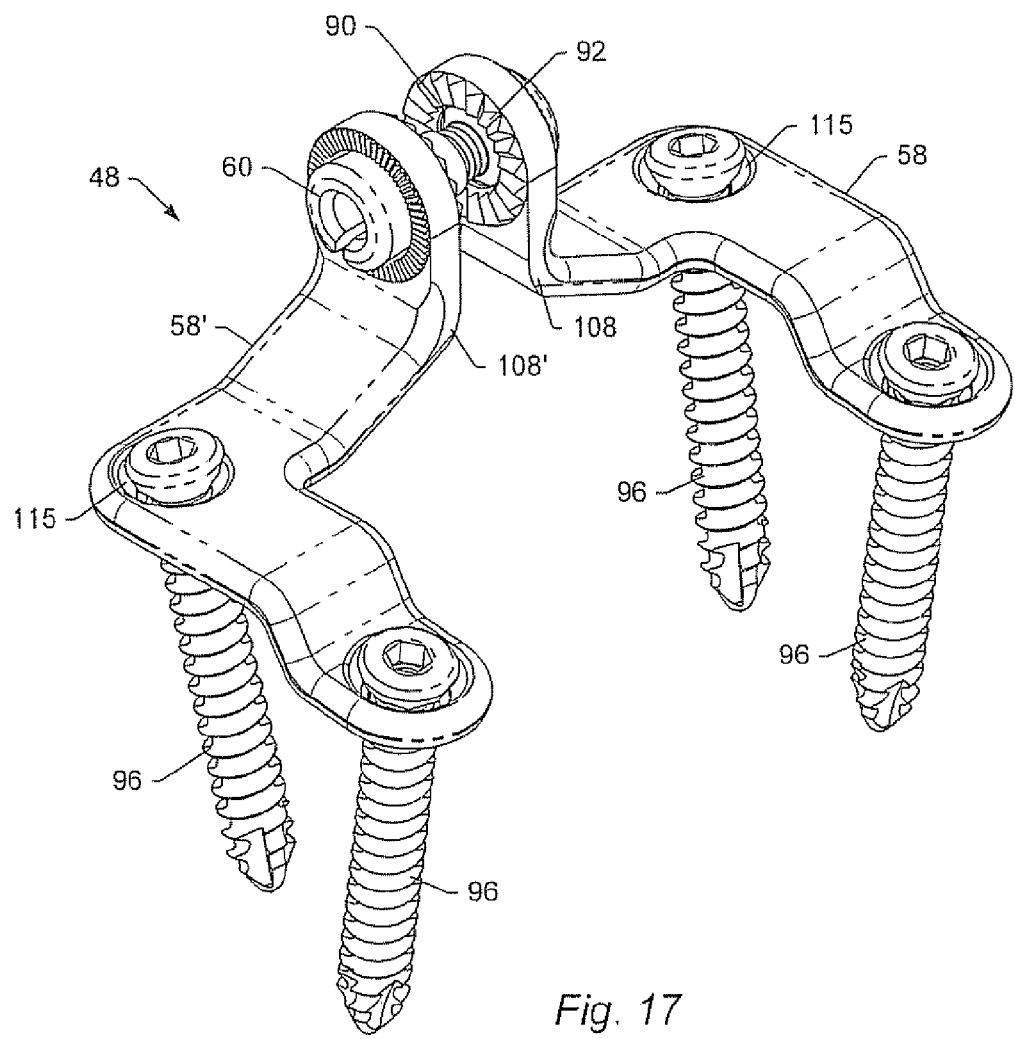
FIG. 17 depicts an embodiment of a spinal stabilization system used to stabilize a portion of the lumbosacral region of the spine.

In FIG. 17, spinal stabilization system 48 may stabilize, for example, the L5 lumbar vertebra and the S1 sacral vertebra of a sacrum. Spinal stabilization system 48 may include structural members 58, connector 60, and fasteners 96. To stabilize adjacent vertebral levels, a portion of first structural member 58' may be positioned adjacent to an inferior articular process of the L5 lumbar vertebra. A second portion of structural member 58' may be positioned adjacent to a surface of the S1 sacral vertebra. Flange 108' may extend from structural member 58' to reside adjacent to a surface of the L5 spinous process. Structural member 58' may be shaped to substantially conform to adjacent vertebral surfaces. Portions of second structural member 58 may be positioned on the opposite inferior articular process of the L5 lumbar vertebra and a second portion of the S1 sacral vertebra. Structural member 58 may include flange 108 positioned adjacent to a surface of the L5 spinous process opposite flange 108'. Structural members 58 may include openings 90 and flange openings 115 for connectors and/or fasteners.

A fastener and/or connector may be positioned through an opening in the structural member to couple the structural member to the vertebra or vertebrae. Referring to FIG. 17, fastener 96 may be positioned through opening 115 in structural member 58' to couple the structural member to the vertebrae and fixate a facet joint between the L5 and S1 vertebrae. A second fastener 96 may be positioned through opening 115 in structural member 58 to couple the structural member to the vertebrae and fixate a second facet joint between the L5 and S1 sacral vertebrae. Other fasteners 96 may be positioned through openings 115 to engage the sacral vertebra and couple structural members 58 to the sacral vertebras. A portion of connector 60 may be positioned through an opening in structural member 58', through a portion of the L5 spinous process, and through opening 90 in structural member 58. Connector 60 couples structural members 58, 58' to the spinous process of the L5 vertebra. Structural members 58, 58' may include serrations on surfaces adjacent to vertebral surfaces to establish a friction and/or form coupling between the structural members and the vertebrae.

Figure 18:
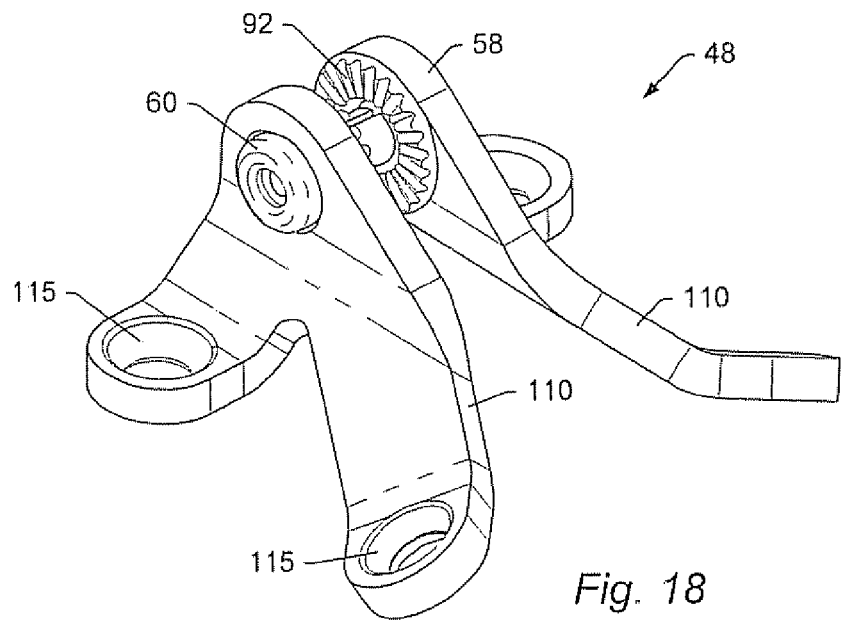
FIG. 18 depicts an embodiment of a spinal stabilization system used to stabilize a portion of the lumbosacral region of the spine.

An embodiment of a spinal stabilization system is depicted in FIG. 18. Spinal stabilization system 48 may include elongated portion 110 extending to a vertebral surface adjacent to a pedicle of a second vertebra. A fastener may pass through opening 115 to engage a portion of the second vertebra and a pedicle. The fastener may couple structural member 58 to the second vertebra.

Figure 19:
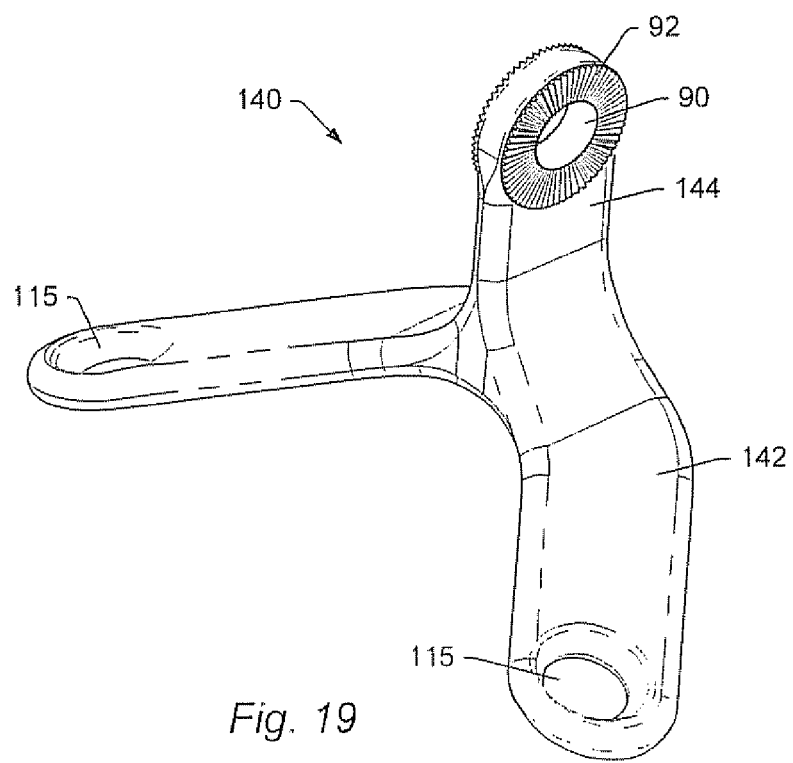
FIG. 19 depicts an embodiment of an artificial spinous process for use with a spinal stabilization system.
Figure 20:
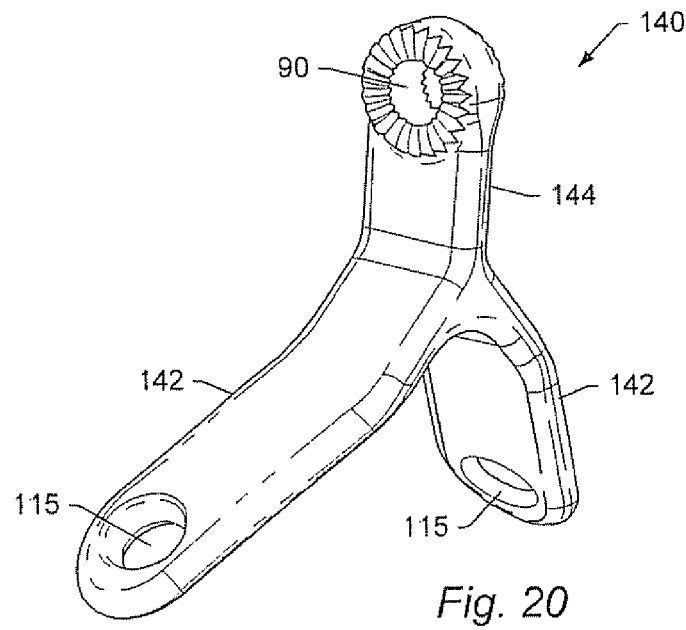
FIG. 20 depicts an embodiment of an artificial spinous process that strengthens or replaces a natural spinous process.

FIG. 19 and FIG. 20 depict embodiments of spinous member 140. Spinous member 140 may be an artificial spinous process that strengthens or replaces a natural spinous process. Spinous member 140 may include base 142 and extending portion 144. Fasteners and/or connectors may couple the spinous member to a vertebra or structural member. Spinous member 140 may be shaped to substantially correspond to adjacent vertebral surfaces and may have flange openings 115 and opening 90 for accepting a fastener and/or connector during use.

Figure 21:
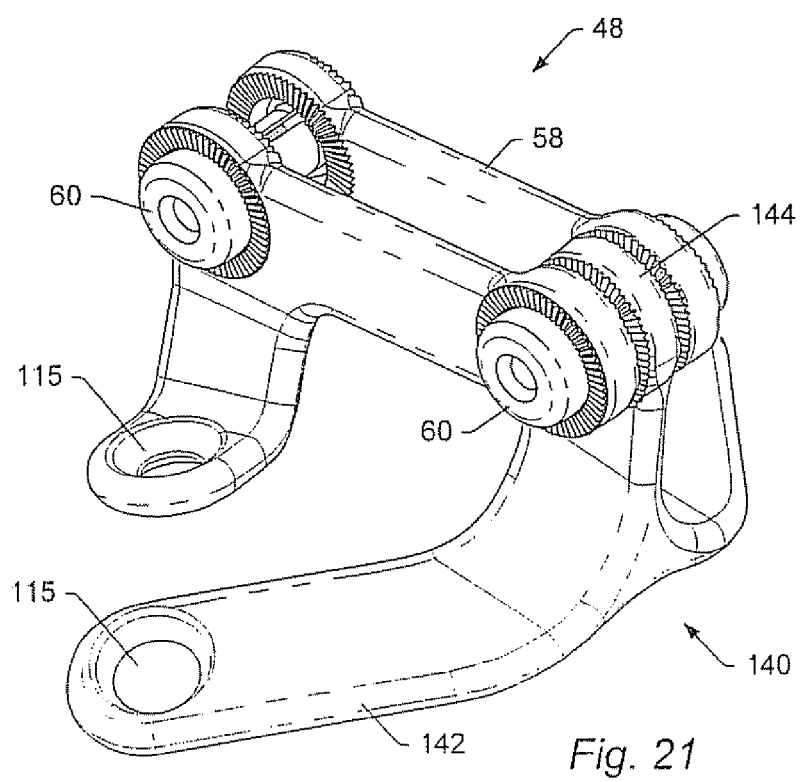
FIG. 21 depicts an embodiment of spinal stabilization system coupled to an artificial spinous process.
Figure 22:
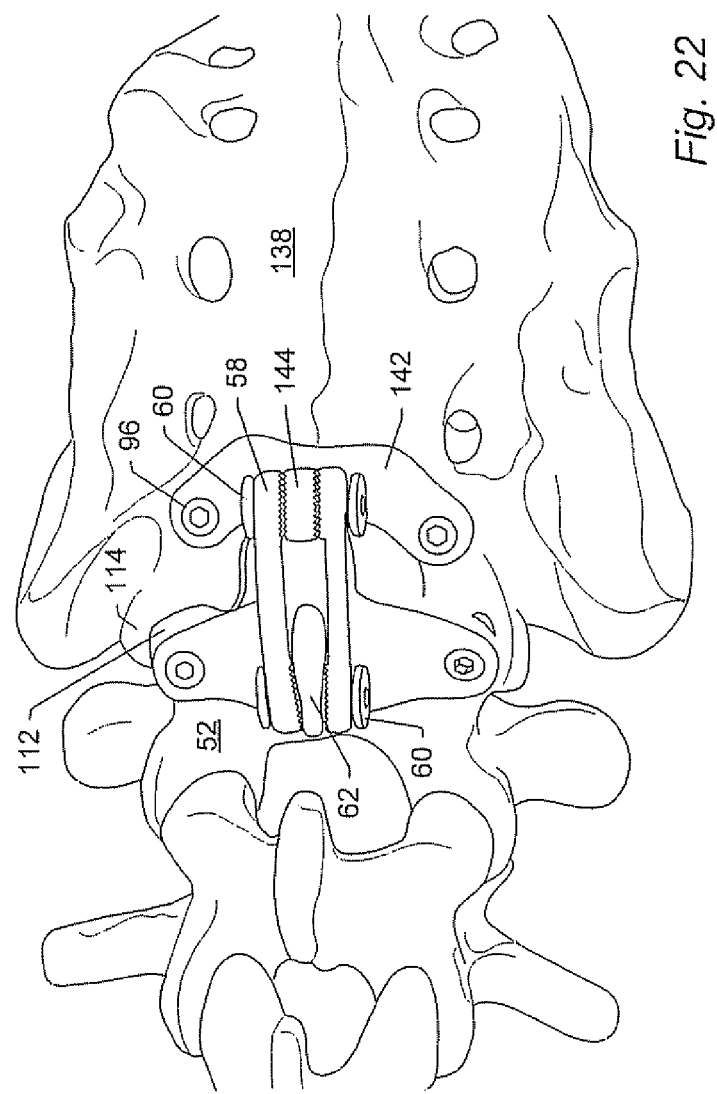
FIG. 22 depicts an embodiment of a spinal stabilization system attached to a human spine for fusing an L5 lumbar vertebra to a sacrum.

FIG. 21 depicts an embodiment of spinal stabilization system 48 coupled to spinous member 140. Spinous member 140 may be used to anchor structural members 58 to a vertebra without a spinous process. Portions of structural members 58 may be positioned on opposing sides of extending portion 144. Openings in the structural members may substantially align with opening 90 in spinous member 140. Connector 60 may be positioned through openings 90 in structural members 58 and spinous member to couple the structural members to spinous member 140. Serrations on the surfaces of the structural members adjacent to the spinous member may couple to mating sensations on a surface of the spinous member to provide a form and/or friction coupling between structural members 58 and spinous member 140. FIG. 22 shows an embodiment of a spinal stabilization system attached to a human spine for fusing an L5 lumbar vertebra 52 to sacrum 138.

Figure 23:
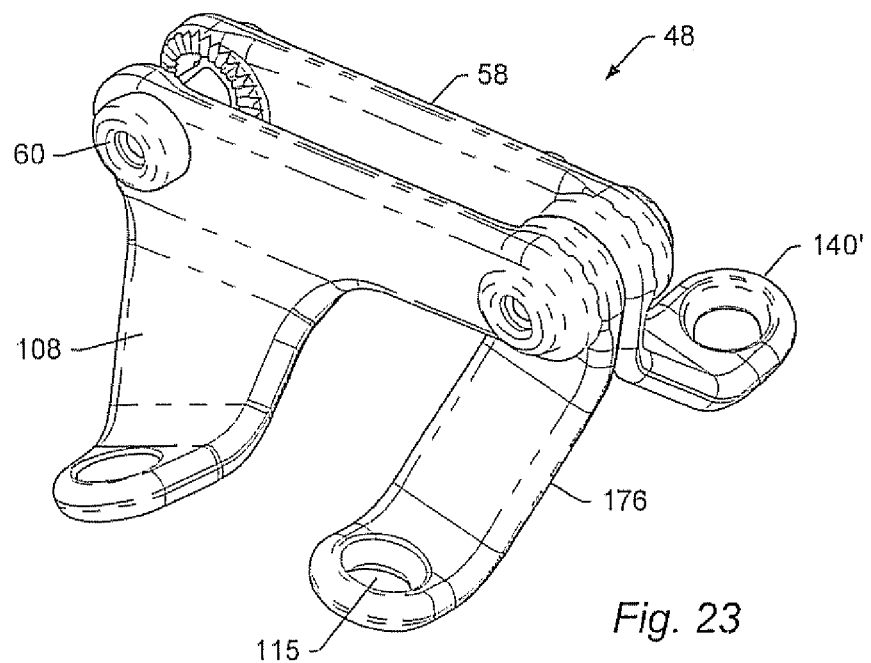
FIG. 23 depicts an embodiment of a spinal stabilization system coupled to artificial spinous members.
Figure 24:
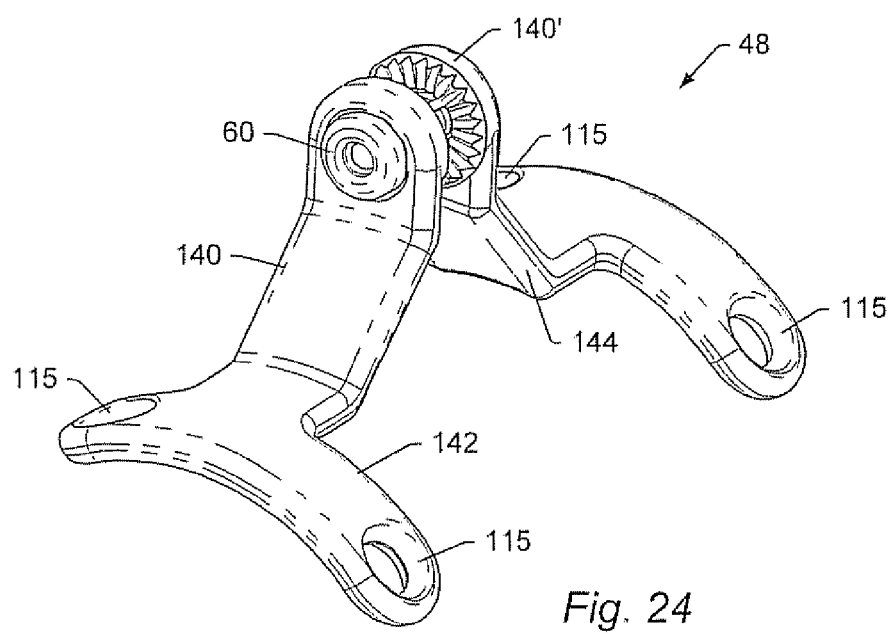
FIG. 24 depicts an embodiment of a spinal stabilization system with an artificial spinous member.
Figure 25:
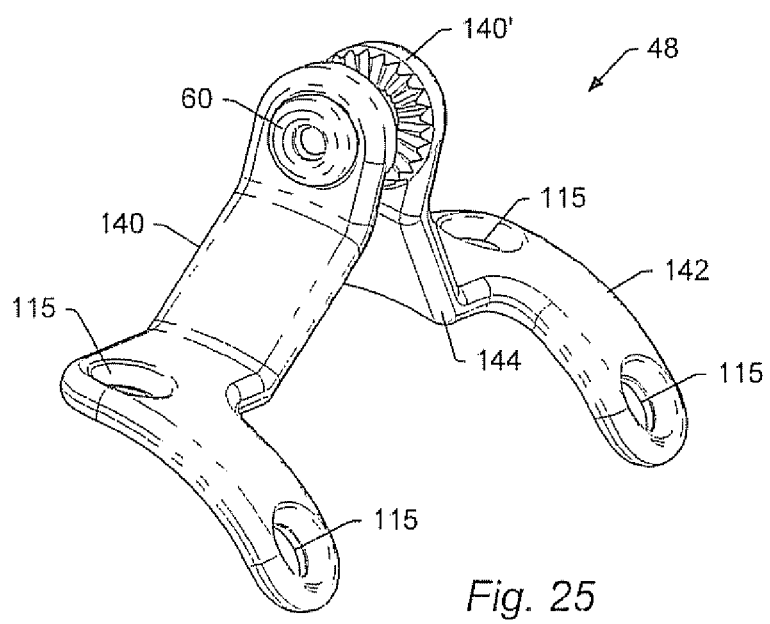
FIG. 25 depicts an embodiment of a spinal stabilization system with an artificial spinous member.

An embodiment of a spinous member may include two opposing members. FIG. 23 through FIG. 25 depict spinal stabilization system 48 having structural members 58, correctors 60, and spinous members 140 and 140'. Spinous members 140 and 140' may be coupled to each other as depicted in FIG. 23 to serve as an artificial spinous process. Alternatively, spinous members 140 and 140' may be coupled to opposite surfaces of a spinous process to provide additional rigidity and support to the spinous process. Texturing on surfaces of the spinous members may enable form and/or friction coupling between adjacent spinous members or between a spinous member and a vertebral surface.

FIG. 24 and FIG. 25 depict embodiments of two-piece spinous members 140, 140' which may be shaped to couple to various individual curvatures and contours of adjacent vertebral surfaces. A pair of openings 115 may be provided at the base of each opposing member for coupling to vertebral surfaces.

Figure 26:
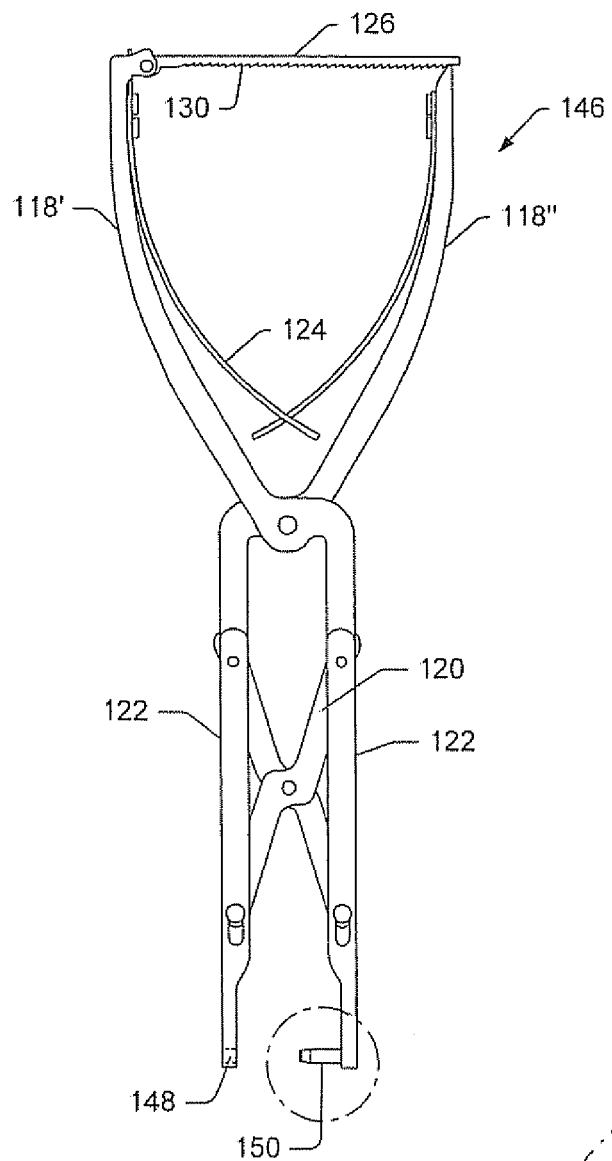
FIG. 26 depicts an embodiment of a punch tool that may be used to form an opening through a spinous process.
Figure 27:
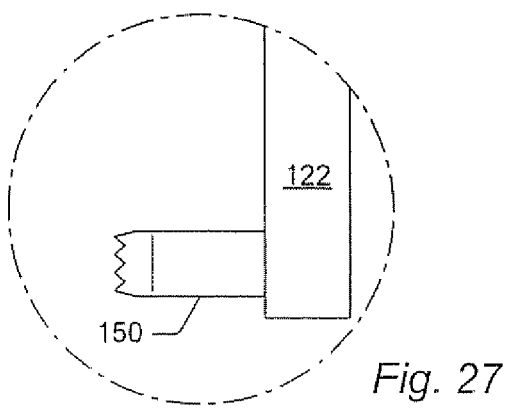
FIG. 27 depicts a detailed view of the hollow cutter used in the punch tool of FIG. 26.

FIG. 26 depicts an embodiment of punch tool 146 that may be used to form an opening through a spinous process. Punch tool 146 may include handles 118, linking mechanism 120, arms 122, spring 124, ratchet arm 126, opening 148, and hollow cutter 150. FIG. 27 depicts a detailed view of the hollow cutter. Opening 148 (represented as hidden lines in FIG. 26) may be placed on one side of a spinous process and cutter 150 may be placed on an opposite side of the spinous process adjacent to a location where an opening is to be formed in the spinous process. Linking mechanism 120 may allow cutter 150 to approach and enter into opening 148 with a small, or no, rotational component of motion of the cutter when handles 118 are squeezed towards each other from an open position. Hollow cutter 150 may cut through the spinous process and form an opening in the spinous process.

Ratchet aim 126 of punch tool 146 may be rotatively attached to first handle 118'. Teeth 130 of ratchet arm 126 may engage an end of second handle 118". Teeth 130 may be oriented to allow handles 118 to approach each other when the handles are squeezed, but the teeth may inhibit the handles from returning to an open position. Spring 124 may apply force to handles 118 that forces the handles to the open position. When an opening in a spinous process has been formed by cutter 150, ratchet arm 126 may be rotated away from the end of second handle 118″ to allow the spring to return the punch tool to the open position. The punch tool may be removed from the patient. Material within hollow cutter 150 and/or opening 148 may be removed.

To stabilize a portion of a spine using a posterior approach, a patient may be prepared, and an incision may be made along a portion of a spine. Tissue may be retracted to expose vertebra 52 that are to be joined together. A template of a first structural member and a template of an opposing structural member may be placed against the vertebrae and molded to desired shapes based on the shape of the patient's vertebrae. The templates may be made of aluminum, aluminum alloy, or other alloy that may be bent with hand pressure to a desired shape for stabilizing the spine. The size of the templates and the size of structural members 58 to be used may be estimated based on radiological images of the patient. After the templates are molded to desired shapes, the templates may be removed from the patient, and corresponding first and second structural members 58 may be formed based on the templates.

Openings for fasteners 96 may be drilled and tapped in vertebrae 52. Fasteners 96 may be used to couple first and second structural members 58 to openings formed in vertebrae 52. A punch tool opening may be placed adjacent to opening 90 through first (or second) structural member 58 that abuts a first spinous process 62. Punch tool 146 may be placed adjacent to a corresponding opening through first (or second) structural member 58. Punch tool handles 118 may be squeezed to form an opening through spinous process 62 between first and second structural members 58. Punch tool 146 may be opened and the material in the hollow cutter 150 and punch opening 148 of punch tool 146 may be removed. An opening in a second spinous process may be formed using punch tool 146.

Connector members 66 and 78 may be attached to holders 128 of connector insertion tool 116. Connector insertion tool 116 may be used to form connector 60 to join structural members 58 together through an opening of first spinous process 62. Connector insertion tool 116 may be used to form connector 60 to join the first and second structural members together through the opening of second spinous process 62 to form a spinal stabilization system.

In some embodiments, a spinal stabilization system may be implanted following an insertion of an interbody fusion device (e.g., spinal implant and/or artificial disc). For example, a spinal implant may be implanted into a patient using an anterior or lateral approach (e.g., anterior lumbar interbody fusion). Following completion of the implant procedure, a spinal stabilization system may be implanted using a posterior approach. Stabilizing the spine in this manner may limit motion of the vertebrae to inhibit separation of vertebrae on an anterior side of the spine. The spinal stabilization system may inhibit movement of the interbody fusion device from the intervertebral space and promote fusion of the device.

A spinal stabilization system may decrease the retraction needed in, as well as minimize the invasiveness, of spinal stabilization. In addition, the use and positioning of fasteners and connectors may further minimize the invasiveness of installation of the spinal stabilization system. As such, risk to the patient may be minimized, and surgical and recovery time may be shortened.

Structural requirements and limitations for spinal fixation may vary at different vertebral levels. Features of the embodiments described herein may be combined to achieve an optimal arrangement for fixating a portion of the spine. The modularity of the structural members and the variety of sizes and shapes available may allow for substantial flexibility in fixating portions of the spine.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for stabilizing a portion of a spine, comprising the steps of:
   making an incision along a portion of a spine;
   retracting tissue to expose vertebrae;
   positioning a surface of a first structural member facing a first side of a first spinous process of a first vertebra and a second spinous process of a second vertebra, the first structural member including a first spike extending from the surface of the first structural member for engagement with the first spinous process and a second spike extending from the surface of the first structural member for engagement with the second spinous process;
   positioning a surface of a second structural member facing a second side of the first spinous process of the first vertebra and the second spinous process of the second vertebra, the first structural member including a third spike extending from the surface of the second structural member for engagement with the first spinous process and a second spike extending from the surface of the second structural member for engagement with the second spinous process;
   positioning a connector which extends between the first structural member and the second structural member between the first spinous process and the second spinous process such that the connector is positioned below the first spinous process and above the second spinous process; and
   drawing the first structural member toward the second structural member such that the spikes of the first and second structural members at least partially penetrate into the first and second spinous processes of the first and second vertebrae.

2. The method of claim 1, further comprising the step of coating the first structural member with a material that promotes osseointegration of the first structural member with the first spinous process.

3. The method of claim 1, wherein the step of positioning a first structural member along a first side of the first spinous process and the second spinous process includes implanting the first structural member using a posterior approach.

4. The method of claim 1, further comprising the step of coupling a third structural member to the first structural member or the second structural member.

5. The method of claim 4, further comprising connecting the third structural member to a third vertebra.

6. The method of claim 1, further comprising the step of implanting an interbody device between the first vertebra and the second vertebra.

7. The method of claim 6, wherein the interbody device is implanted between the first vertebra and the second vertebra in an anterior or lateral approach.

8. A method for stabilizing a portion of a spine, comprising the steps of:
- making an incision along a portion of a spine;
- retracting tissue to expose a spinous process of a first vertebra and a spinous process of a second vertebra;
- positioning a first textured surface of a first structural member facing a first side of the spinous process of the first vertebra and a second textured surface of the first structural member facing a first side of the spinous process of the second vertebra, the first textured surface of the first structural member located at a first end portion of the first structural member and the second textured surface of the first structural member located at a second end portion of the first structural member;
- positioning a first textured surface of a second structural member facing a second side of the spinous process of the first vertebra and a second textured surface of the second structural member facing a second side of the spinous process of the second vertebra, the first textured surface of the second structural member located at a first end portion of the second structural member and the second textured surface of the second structural member located at a second end portion of the second structural member;
- positioning a connector between the first spinous process and the second spinous process such that the connector is positioned below the first spinous process and above the second spinous process, the connector extending from an intermediate location of the first structural member to an intermediate location of the second structural member, the intermediate location of the first structural member located between the first and second textured surfaces of the first structural member, and the intermediate location of the second structural member located between the first and second textured surfaces of the second structural member; and
- drawing the first structural member toward the second structural member such that the first and second spinous processes are pressed therebetween and the first textured surfaces of the first and second structural members penetrate into the first and second sides of the spinous process of the first vertebra and the second textured surfaces of the first and second structural members penetrate into the first and second sides of the spinous process of the second vertebra.

9. The method of claim 8, further comprising the step of coating the first structural member with a material that promotes osseointegration of the first structural member with the spinous process.

10. The method of claim 8, wherein the step of positioning a first structural member along a first side of the spinous process includes implanting the first structural member using a posterior approach.

11. The method of claim 8, further comprising the step of coupling a third structural member to the first structural member or the second structural member.

12. The method of claim 11, further comprising connecting the third structural member to a third vertebra.

13. The method of claim 8, further comprising the step of implanting an interbody device between the first vertebra and the second vertebra.

14. The method of claim 13, wherein the interbody device is implanted between the first vertebra and the second vertebra in an anterior or lateral approach.

15. A method for stabilizing a portion of a spine, comprising the steps of:
- making an incision along a portion of a spine;
- retracting tissue to expose a spinous process of a first vertebra and a spinous process of a second vertebra;
- installing a spinal fixation system onto the first and second vertebrae with a first structural member of the spinal fixation system facing a first side of the spinous process of the first vertebra and facing a first side of the spinous process of the second vertebra, a second structural member of the spinal fixation system facing a second side of the spinous process of the first vertebra and facing a second side of the spinous process of the second vertebra, and an intermediate connector that extends from the first structural member to the second structural member at a location between the spinous process of the first vertebra and the spinous process of the second vertebra without the intermediate connector extending through a spinous process; and
- drawing the first structural member toward the second structural member such that the first and second spinous processes are pressed therebetween and spikes of the first and second structural members penetrate into the first and second sides of the spinous process of the first vertebra and spikes of the first and second structural members penetrate into the first and second sides of the spinous process of the second vertebra.

16. The method of claim 15, wherein the first structural member includes spikes at a first end portion and a second end portion of the first structural member, and the second structural member includes spikes at a first end portion and second end portion of the second structural member.

17. The method of claim 16, wherein the intermediate connector is connected to the first structural member at an intermediate location between the first end portion and the second end portion of the first structural member, and the intermediate connector is connected to the second structural member at an intermediate location between the first end portion and the second end portion of ht second structural member.

* * * * *

UNITED STATES PATENT AND TRADEMARK OFFICE
CERTIFICATE OF CORRECTION

| | | |
|---|---|---|
| PATENT NO. | : 8,439,953 B2 | Page 1 of 1 |
| APPLICATION NO. | : 11/779762 | |
| DATED | : May 14, 2013 | |
| INVENTOR(S) | : Margaret E. Mitchell et al. | |

It is certified that error appears in the above-identified patent and that said Letters Patent is hereby corrected as shown below:

In the Specification

Column 8, Line 17: delete "members" and insert -- member --.

Column 14, Line 20: delete "sensations" and insert -- serrations --.

Signed and Sealed this
Third Day of December, 2013

Margaret A. Focarino
*Commissioner for Patents of the United States Patent and Trademark Office*